US012502563B2

(12) United States Patent

Kimbahune et al.

(10) Patent No.: US 12,502,563 B2

(45) Date of Patent: Dec. 23, 2025

(54) SYSTEM AND METHOD FOR CONTEXT AWARE NETWORKED MASK WITH DYNAMIC AIR IMPEDANCE FOR OPTIMUM BREATHABILITY

(71) Applicant: Tata Consultancy Services Limited, Mumbai (IN)

(72) Inventors: Sanjay Madhukar Kimbahune, Thane (IN); Avik Ghose, Kolkata (IN); Sujit Raghunath Shinde, Thane (IN); Ashish Indani, Mumbai (IN); Devraj Goulikar, Mumbai (IN); Swarnava Dey, Kolkata (IN)

(73) Assignee: TATA CONSULTANCY SERVICES LIMITED, Mumbai (IN)

(*) Notice: Subject to any disclaimer, the term of this patent is extended or adjusted under 35 U.S.C. 154(b) by 1051 days.

(21) Appl. No.: 17/643,041

(22) Filed: Dec. 7, 2021

(65) Prior Publication Data

US 2022/0233896 A1 Jul. 28, 2022

(51) Int. Cl.

*G16H 50/30* (2018.01)
*A62B 18/08* (2006.01)

(Continued)

(52) U.S. Cl.

CPC ............ *A62B 18/08* (2013.01); *A62B 23/025* (2013.01); *G16H 40/67* (2018.01); *G16H 50/30* (2018.01); *B01D 2275/302* (2013.01)

(58) Field of Classification Search

None

See application file for complete search history.

(56) References Cited

U.S. PATENT DOCUMENTS

| | | | | |
|---|---|---|---|---|
| 10,561,863 | B1 * | 2/2020 | Dashevsky | A61B 5/6803 |
| 2011/0030127 | A1 * | 2/2011 | Dias | D04B 1/24 66/170 |

(Continued)

FOREIGN PATENT DOCUMENTS

| | | | |
|---|---|---|---|
| CN | 108271121 | A | 7/2018 |
| KR | 20160002280 | A | 1/2016 |
| WO | WO2017204395 | A1 | 11/2017 |

OTHER PUBLICATIONS

Naren Vikram Raj Masna et al., "The Smart Mask: Active Closed-Loop Protection against Airborne Pathogens", Signal Processing, Sep. 2020, Arxiv, Link: https://arxiv.org/pdf/2008.10420.pdf.

*Primary Examiner* — Bradley H Philips

(74) *Attorney, Agent, or Firm* — Finnegan, Henderson, Farabow, Garrett & Dunner, LLP

(57) ABSTRACT

While facing polluted environments one does not need extreme breath filtering protection all the time. Methods of the art hardly focus on breathability aspect while working on smart masks. Embodiments of the present disclosure provide a system and method for context aware networked mask with dynamic air impedance for optimum breathability. The system provides a smart mask that regulates the air inlet (by modulating the position/pore size of filtering membrane or by using resizable gel) as per the prevalent risk at that instance. The context aware mask with a mesh network, disclosed herein, comprises sensors and processing unit, which use contextual information and Artificial Intelligence to develop models for generating alerts along with mechanism of dynamically regulating the pore size to ensure breathability by adjusting air impedance.

10 Claims, 7 Drawing Sheets

(51) Int. Cl.
*A62B 23/02* (2006.01)
*G16H 40/67* (2018.01)

(56) References Cited

U.S. PATENT DOCUMENTS

| | | | | |
|---|---|---|---|---|
| 2013/0104733 | A1* | 5/2013 | Bangera | A62B 23/025 128/206.12 |
| 2016/0029716 | A1* | 2/2016 | Duncan | A41D 13/11 128/863 |
| 2018/0078798 | A1* | 3/2018 | Fabian | A62B 18/10 |
| 2018/0256926 | A1 | 9/2018 | Kyung et al. | |
| 2018/0325422 | A1* | 11/2018 | Sokol | A62B 7/10 |
| 2023/0284714 | A1* | 9/2023 | Chahine | A41D 13/11 |

* cited by examiner

Set of 4 MEMS without control signal

SYSTEM AND METHOD FOR CONTEXT AWARE NETWORKED MASK WITH DYNAMIC AIR IMPEDANCE FOR OPTIMUM BREATHABILITY

PRIORITY CLAIM

This U.S. patent application claims priority under 35 U.S.C. § 119 to: the Indian application no. 202121003902, filed on Jan. 28, 2021. The entire contents of the aforementioned application are incorporated herein by reference.

TECHNICAL FIELD

The embodiments herein generally relate to smart masks and, more particularly, to a system and method for context aware networked mask with dynamic air impedance for optimum breathability.

BACKGROUND

It has been predicted that masks will be part of everyday life for an extended period, post Covid-19 pandemic era. Masks offer some level of protection against virus. Masks filter out pathogenic particles. As viruses are very small, it is imperative to have reasonably small pore size along with other factors like static charges. It has been observed that prolonged use of mask leads to many issues. For people with breathing difficulties, it is a bigger challenge. Masks like N95 are worn because of fear, however their breathability is also troublesome for common people who are not accustomed to wearing N95 masks. Masks, if worn while exercising, can cause havoc to health. Some masks offer breather unit, but their efficacy is questioned by healthcare community especially for transmitting the virus to others. Thus, it is more comfortable for a user to wear a right mask for a right scenario. However, maintaining multiple masks and rightly identifying the appropriate type of mask to be worn for a current environment is practically challenging for a general user. Moreover, selection of appropriate mask is very much dependent on the health state of the individual and a generalized approach may not be convenient or comfortable to each individual.

Research carried out on smart masks introduce smartness in different contexts and perspectives. One of the existing methods focusses on smartly alerting user by identifying possibility of infectious crowd around, while some other smart masks intelligently guide user through a least polluted route by monitoring the air quality in the ambient environment. Some existing works disclose capability to alert user based on degrading quality of the filter, while other works discuss on intelligent masks that auto trigger cleaning of residual particles settled on the filter area of the mask, with appropriate alerts and suggestions to the user. However, hardly any attempts have been made to introduce smartness in context of breathability of the mask in terms of air impedance variations.

SUMMARY

Embodiments of the present disclosure present technological improvements as solutions to one or more of the above-mentioned technical problems recognized by the inventors in conventional systems.

For example, a system for context aware networked mask with dynamic air impedance for optimum breathability is provided. The system comprises a mask comprising a base material attached with holding strings at two ends, wherein the base material holds: a mesh network having one or more layers with a pore diameter associated with each of the one or more layers, wherein each of the one or more layers are held by an actuator applying a stretch force on each of the one or more layers; a plurality of sensors, attached to the base material, and comprising a plurality of air quality sensors for sensing a plurality of environmental parameters and a plurality of biological sensors for sensing a plurality of biological parameters of a wearer of the mask; a communication interface attached to the base material and configured to a) transmit the sensed plurality of environmental parameters and the biological parameters to a master device and b) receive a customized risk score from the master device; and an actuator unit configured to process the customized risk score received from the communication module to generate an actuation signal that varies the stretch force applied by the actuator on each of the one or more layers in accordance to the customized risk score to vary resultant air impedance of the mesh network by varying effective pore diameter to adjust breathability for the wearer; the master device comprising: a memory storing instructions; one or more Input/Output (I/O) interfaces; and one or more hardware processors coupled to the memory via the one or more I/O interfaces, wherein the one or more hardware processors are configured by the instructions to: process, via an AI based Real time risk calculation module in the memory implemented by the one or more hardware processors, a) the plurality of environmental parameters, the plurality of biological parameters, ambient environment and context data of the wearer, meta data of the wearer and user inputs to generate the customized risk score; and b) generate alerts for the wearer in accordance to the customized risk score and a set of predefined rules.

The master device is configured to communicate with a cloud server 106 for computationally intensive processing to derive health insights from historical data comprising customized risk scores, the meta data of the wearer, the plurality of biological parameters, the plurality of environmental parameters.

In another aspect, in one embodiment, a method for context aware networked mask with dynamic air impedance for optimum breathability is provided. The method includes receiving, by one or more hardware processors of a master device, a plurality of environmental parameters and a plurality of biological parameters sensed by a plurality of sensors of a mask. Further the method comprises processing, via an AI based Real time risk calculation module implemented by the one or more hardware processors, the plurality of environmental parameters, the plurality of biological parameters, ambient environment and context data of a wearer of the mask, meta data of the wearer and user inputs to generate a customized risk score. Furthermore the method comprises communicating, via the one or more hardware processors, the customized risk score to an actuator unit of the mask, wherein actuator unit processes the customized risk score to generate an actuation signal that varies a stretch force applied by an actuator on each of one or more layers of a mesh network of the mask in accordance with the customized risk score to vary effective pore diameter of the mesh network, which in turn varies resultant air impedance to adjust breathability for the wearer. Furthermore, the method comprises generating, via the one or more hardware processors, alerts for the wearer in accordance with the customized risk score and a set of predefined rules.

The method further comprising communicating with a cloud server for computationally intensive processing to derive health insights from historical data comprising customized risk scores, the meta data of the wearer, the biological plurality of parameters, the plurality of environmental parameters.

In yet another aspect, there are provided one or more non-transitory machine-readable information storage mediums comprising one or more instructions, which when executed by one or more hardware processors causes a method for context aware networked mask with dynamic air impedance for optimum breathability is provided. The method comprises receiving of a master device, a plurality of environmental parameters and a plurality of biological parameters sensed by a plurality of sensors of a mask. Further the method comprises processing, via an AI based Real time risk calculation module the plurality of environmental parameters, the plurality of biological parameters, ambient environment and context data of a wearer of the mask, meta data of the wearer and user inputs to generate a customized risk score. Furthermore the method comprises communicating the customized risk score to an actuator unit of the mask, wherein actuator unit processes the customized risk score to generate an actuation signal that varies a stretch force applied by an actuator on each of one or more layers of a mesh network of the mask in accordance with the customized risk score to vary effective pore diameter of the mesh network, which in turn varies resultant air impedance to adjust breathability for the wearer. Furthermore, the method comprises generating alerts for the wearer in accordance with the customized risk score and a set of predefined rules. The method further comprising communicating with a cloud server for computationally intensive processing to derive health insights from historical data comprising customized risk scores, the meta data of the wearer, the biological parameters, the plurality of environmental parameters.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

Figure 1:
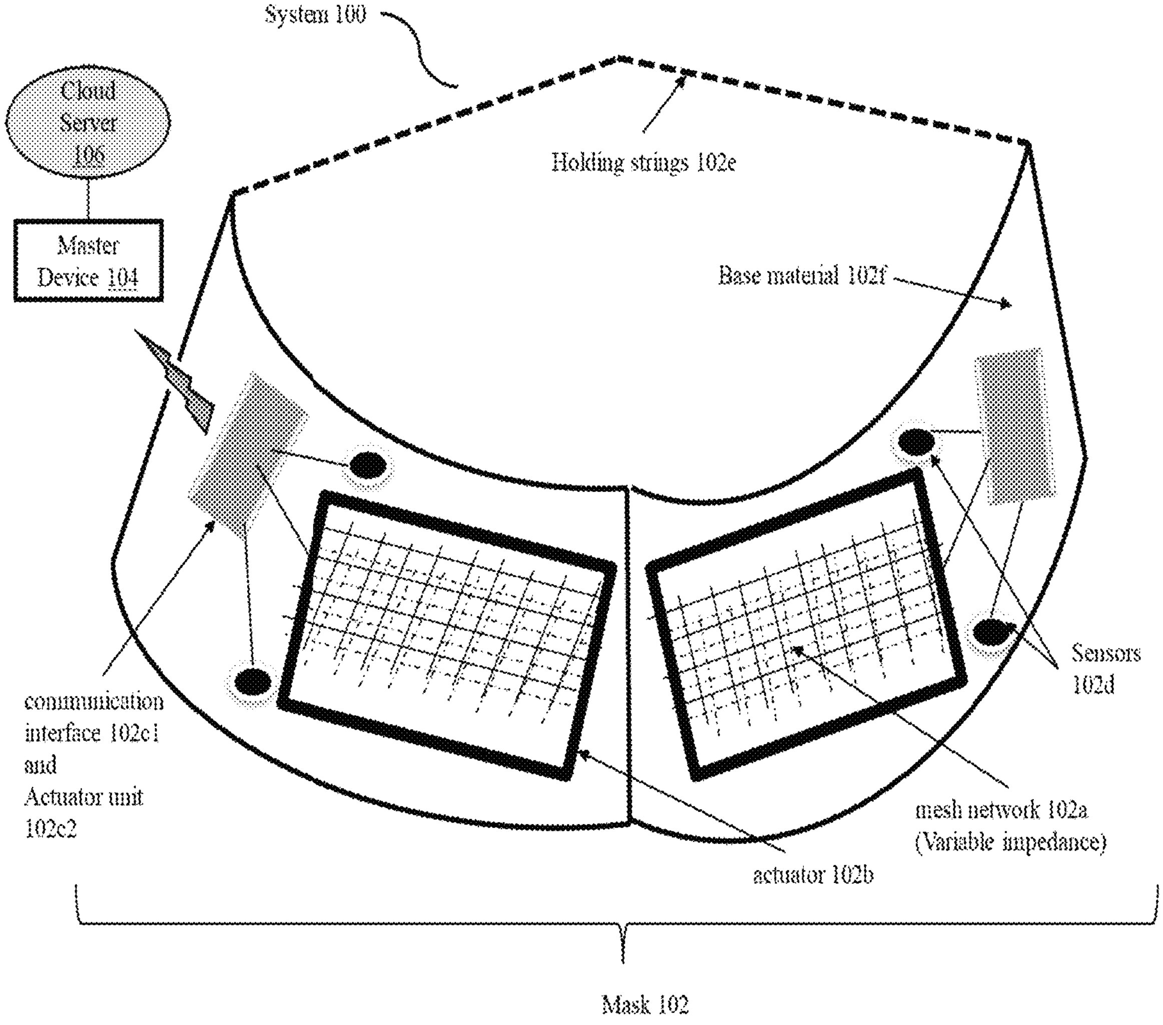
FIG. 1 is an overview of a system for context aware networked mask with dynamic air impedance for optimum breathability, in accordance with some embodiments of the present disclosure.

It should be appreciated by those skilled in the art that any block diagrams herein represent conceptual views of illustrative systems and devices embodying the principles of the present subject matter. Similarly, it will be appreciated that any flow charts, flow diagrams, and the like represent various processes which may be substantially represented in computer readable medium and so executed by a computer or processor, whether or not such computer or processor is explicitly shown.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

While facing polluted environments one does not need extreme breath filtering protection all the time. It is dependent on many factors such as immunity of the person, type of pollutants around, current physical state of the person and the like. Methods of the art hardly focus on breathability aspect while working on smart masks. Embodiments of the present disclosure provide a system and method for context aware networked mask with dynamic air impedance for optimum breathability. The system provides a smart mask that regulates the air inlet (by modulating the position/pore size of filtering membrane or by using resizable gel) as per the prevalent risk at that instance. The context aware mask with a mesh network, disclosed herein, comprises sensors and processing unit, which use contextual information and Artificial Intelligence to develop models for generating alerts along with mechanism of dynamically regulating the pore size to ensure breathability by adjusting air impedance.

Referring now to the drawings, and more particularly to FIGS. 1 through 5, where similar reference characters denote corresponding features consistently throughout the figures, there are shown preferred embodiments and these embodiments are described in the context of the following exemplary system and/or method.

FIG. 1 is an overview of a system 100 for context aware networked mask with dynamic air impedance for optimum breathability, in accordance with some embodiments of the present disclosure. The system 100 includes a mask 102 worn by a wearer, a master device 104 owned by the wearer and in proximity of the mask and a cloud server 106 connected to the master device 104 through long range communication networks such as cellular or the like. The system 100 provides a smart network enabled mask that is aware of wearers' biological parameters and environment around him. The system 100 dynamically changes the air impedance of the mask 102 based on the context such as risk posed current ambient environment of the wearer in accordance individuals current health state, meta data of the wearer gathered over time and so on. Sensors 102*d* placed on the mask 102 sense the environment from within the mask as well as outside the mask. A communication interface 102*c*1 facilitates smooth data exchange across the sensors 102*d* and the master device 104. Based on user's (wearer's) meta data, instantaneous sensor readings, past historical data and Artificial Intelligence (AI) based processing in the master device 104, appropriate alerts are issued to the wearer. The master device 104 is installed with a mobile app for data entry, visualization and alerting. The master device 104 can be a smart phone, a personal digital assistant or any other device capable of processing the data using AI based modules and communicating with the cloud server 106.

In safety critical deployments e.g. workers in hazardous environment, immune-compromised patients, the master device 104 may need to process data from different orthogonal sensors, with multiple time series streams and generate inference. One artificial intelligence model cannot be trained for all such sensors. Thus, a set of AI models is required. These require resources and computation power even greater than that can be supported by the master device 104, such as the smart phone. Given that the lower level reorientations for timeseries signature classification is fairly generic, multi objective neural networks can be optimized fixing set of lower layers and a set of high-level layers that can be transfer learned/fine-tuned for each sensor. The determination of this partition is not trivial and is based on the desired latency, processing, memory and also the accuracy especially false negatives that may have telling effect on user health. This optimization is formulated and implemented it in the AI based risk calculation module 210 The AI based risk calculation module 210 can be generated in cloud server and then transferred on the master device 104. The data from the external sensors could be utilized to build super granular air quality/pathogen presence maps in a given area. Such masks would not only enable user to safely navigate through contaminated/risk prone areas, but allow better breathing through mask, when the user is in a relatively safer area.

Referring now to the system of FIG. 1, the mask 102 comprises a base material 102*f* attached with holding strings 102*e* at two ends. The base material can be chosen to be any skin friendly flexible material such as cloth or polymer. The base material 102*f* holds: a mesh network (102*a*) having one or more layers with a predefined pore size associated with each of the one or more layers, wherein each of the one or more layers is held by an actuator 102*b* by applying a stretch force on each of the one or more layers. The mesh network can be:

a) A mesh of closely knit polymer with elastic properties, wherein average or effective pore diameter of the closely knit polymer increases with the increasing stretch force applied by the actuator unit allowing more air to enter the mask for increased breathability.

b) A multi-layered mesh with pore diameters (interchangeably referred as pore sizes) larger than the closely knit polymer, wherein layers of the mesh are overlaid on each other, and wherein the actuator unit is configured to realign the pores of each layer in accordance with the actuator control signal to vary the resultant pore size of the multi-layered mesh changing the air impedance and modulating the breathability.

A plurality of sensors 102*d* are attached to the base material 102*f*. The sensors 102*d* are broadly of two types, a plurality of air quality sensors for sensing a plurality of environmental parameters and a plurality of biological sensors for sensing plurality of biological parameters of the wearer. The air quality sensors comprise pathogen sensors, pollen grain sensors, Volatile Organic Compounds (VOC) sensors, bacteria sensors, ear lobe based PPG sensors and mold sensors. The biological sensors comprise CO2 sensors, temperature sensors, SPO2 and moisture sensors.

The communication interface (102*c*1) attached to the base material (102*f*) is configured to a) transmit the sensed environmental parameters and the biological parameters to a master device and b) receive a customized risk score from the master device. The risk score computation is performed on the master device 104 and is explained later in conjunction with FIG. 5.

A small actuator unit (102*c*2) is mounted on the mask and is configured to process the customized risk score received from the communication module (102*c*1) to generate an actuation signal. The actuation signal varies say a voltage signal that further varies the stretch force applied by the actuator on each of the one or more layers in accordance with the customized risk score. This stretch force varies the pore diameter of the one or more layers, effectively varying resultant air impedance of the mesh network to adjust breathability for the wearer. The actuator is a precision actuator such as Micro ElectroMechanical System (MEMS), piezoelectric crystals or bimetallic strips. An example single layer mesh network with actuator assembly and construction is shown in FIGS. 3A through 3C, and FIGS. 4A through 4E depict a multi-layered mech network with the actuator assembly.

Further, the mask 102 can communicate with the master device 104 configured to process, via an AI based Real time risk calculation module a) the plurality of environmental parameters, the plurality of biological parameters, ambient environment and context data of the wearer, meta data of the wearer and user inputs to generate the customized risk score; and b) generate alerts for the wearer in accordance to the customized risk score and a set of predefined rules. Further, the master device 104 is configured to communicate with a cloud server 106 for computationally intensive processing to derive health insights from historical data comprising customized risk scores, the meta data of the wearer, the plurality of biological parameters, the plurality of environmental parameters.

Figure 2:
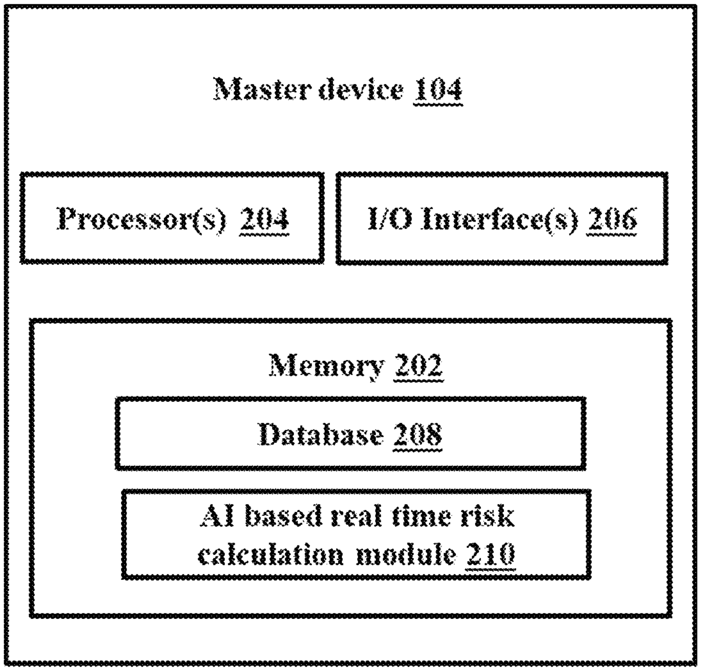
FIG. 2 is a functional block diagram of a master device of the system of FIG. 1 for context aware networked mask with dynamic air impedance for optimum breathability, in accordance with some embodiments of the present disclosure.

FIG. 2 is a functional block diagram of a master device of the system of FIG. 1 for context aware networked mask with dynamic air impedance for optimum breathability, in accordance with some embodiments of the present disclosure.

In an embodiment, the master device 102 includes a processor(s) 204, communication interface device(s), alternatively referred as input/output (I/O) interface(s) 206, and one or more data storage devices or a memory 202 operatively coupled to the processor(s) 204. The master device 102 with one or more hardware processors is configured to execute functions of one or more functional blocks of the master device 102. Referring to the components of the master device 102, in an embodiment, the processor(s) 204, can be one or more hardware processors 204. In an embodiment, the one or more hardware processors 204 can be implemented as one or more microprocessors, microcomputers, microcontrollers, digital signal processors, central processing units, state machines, logic circuitries, and/or any devices that manipulate signals based on operational instructions. Among other capabilities, the one or more hardware processors 204 are configured to fetch and execute computer-readable instructions stored in the memory 202. In an embodiment, the system 100 can be implemented in a variety of computing systems including laptop computers, notebooks, hand-held devices such as mobile phones, workstations, mainframe computers, servers, and the like.

The I/O interface(s) 206 can include a variety of software and hardware interfaces, for example, a web interface, a graphical user interface to display the generated target images and the like and can facilitate multiple communications within a wide variety of networks N/W and protocol types, including wired networks, for example, LAN, cable, etc., and short range and long range wireless networks, such as WLAN, cellular, Wi-Fi, Bluetooth and the like. In an embodiment, the I/O interface (s) 206 can include one or more ports for connecting to a number of external devices or to another server such as cloud server 106 or devices. The I/O interface 206 enables short range communication enabling the master device 102 to have a two way connection with the mask for receiving the sensed biologicals parameters and the environmental parameters and sharing the customized health risk score computed based on the parameter values for the ambient environment the wearer of the mask is in. In an embodiment, the master device 102 may utilize the cloud servers such as cloud server 106 for computationally intensive processing to derive health insights from historical data comprising customized risk scores, the meta data of the wearer, the biological parameters, the environmental parameters.

The memory 202 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes.

Further, the memory 202 may include an AI based Real time risk calculation module 210 that is configured to compute the customized risk score for the wearer in the current ambient environment. Further, memory 202 includes a database 208 that stores the received plurality of biological parameters, the plurality of environmental parameters, the computed customized risk scores, the generated alerts and the like. The memory 202 may comprise information pertaining to input(s)/output(s) of each step performed by the processor(s) 204 of the master device 102 and methods of the present disclosure. In an embodiment, the database 208 may be external (not shown) to the master device 102 and coupled via the I/O interface 206. Functions of the components of the master device 102 are explained in conjunction with flow diagram of FIG. 5 and system of FIG. 1.

Figure 3A:
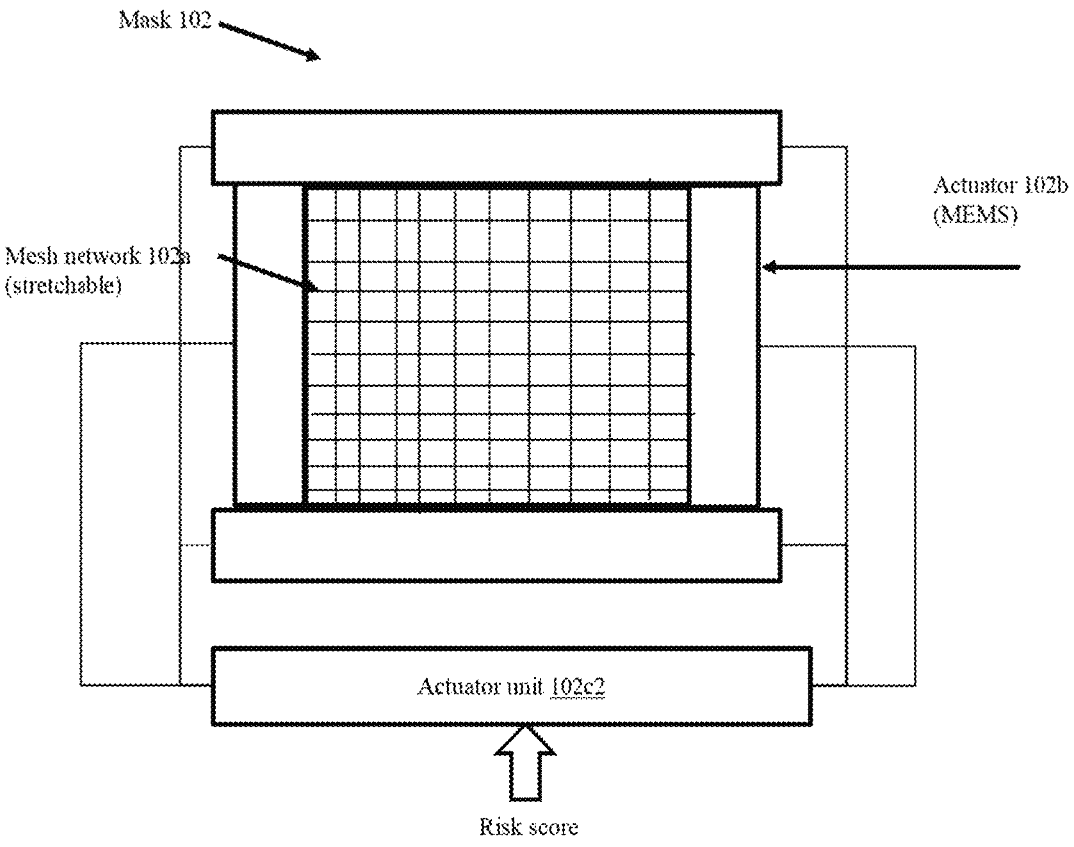
FIG. 3A is a first illustrative example of a single layered mesh network used in the mask of the system of FIG. 1, in accordance with some embodiments of the present disclosure.
Figure 3B:
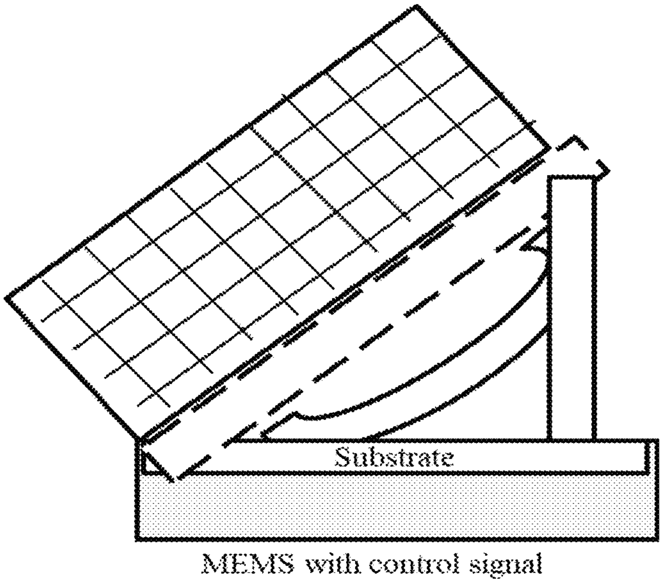
FIG. 3B is a second illustrative example of a single layered mesh network used in the mask of the system of FIG. 1, in accordance with some embodiments of the present disclosure.
Figure 3C:
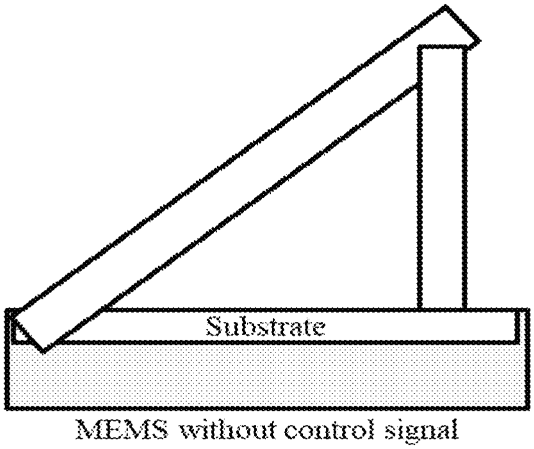
FIG. 3C is a third illustrative example of a single layered mesh network used in the mask of the system of FIG. 1, in accordance with some embodiments of the present disclosure.

FIG. 3A through 3C (collectively referred as FIG. 3) is an illustrative example of a single layered mesh network used in the mask of the system of FIG. 1, in accordance with some embodiments of the present disclosure.

FIG. 4A through 4E (collectively referred as FIG. 4) is an illustrative example of a multi-layered mesh network used in the mask of the system of FIG. 1, in accordance with some embodiments of the present disclosure.

The design and working of single layered and multi-layered mesh is based on same principle. Explained below is the example design of four layered mesh of FIG. 4.

The dimensional aspects of pollutants and mask: Typical sizes of pollen grains is from 15 to 200 micrometers and bacteria are from 0.3 to 2 micrometers, Suspended Particulate matter (SPM) is approx. 2.5 micrometers, whereas viruses are from 0.5 to 300 nanometers. Surgical masks use non-woven material whose average pore size is 0.3 to 10 micrometers where as N95 masks have an average pore size of 0.1 to 0.3 micrometers. Additionally, there is a layer of statically charged material that helps in trapping the pathogens/pollutants.

Figure 4A:
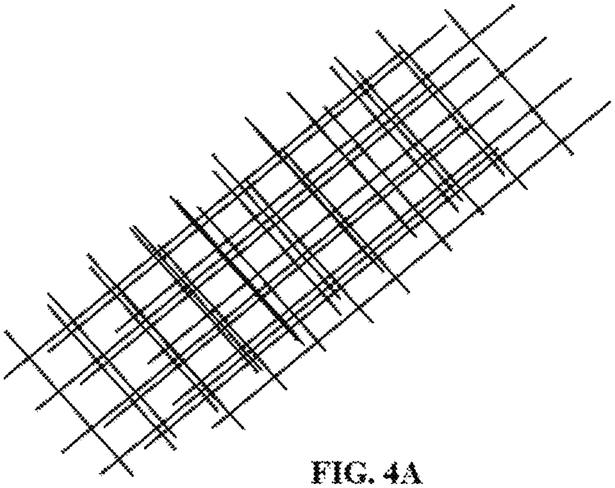
FIG. 4A is a first illustrative example of a multi-layered mesh network used in the mask of the system of FIG. 1, in accordance with some embodiments of the present disclosure.
Figure 4B:
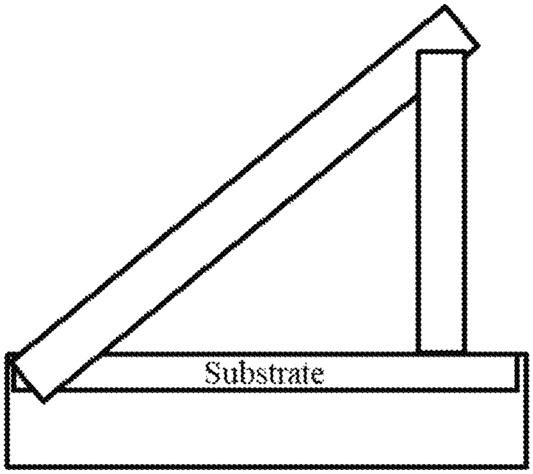
FIG. 4B is a second illustrative example of a multi-layered mesh network used in the mask of the system of FIG. 1, in accordance with some embodiments of the present disclosure.
Figure 4C:
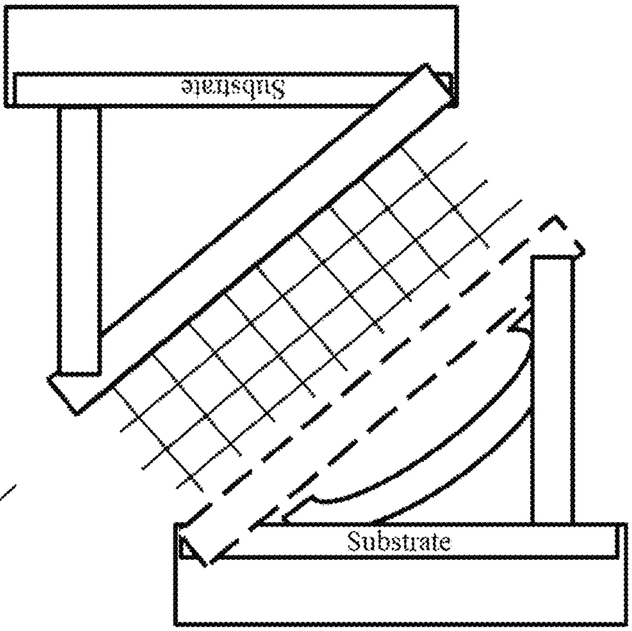
FIG. 4C is a third illustrative example of a multi-layered mesh network used in the mask of the system of FIG. 1, in accordance with some embodiments of the present disclosure.
Figure 4D:
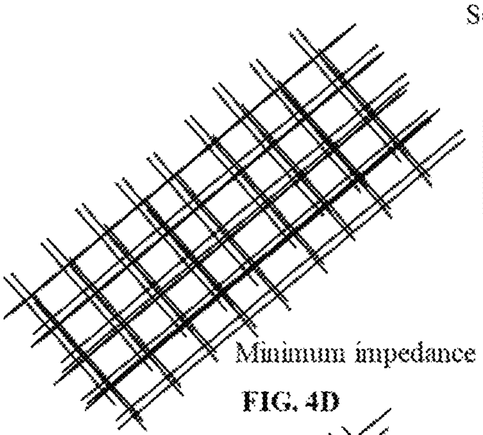
FIG. 4D is a fourth illustrative example of a multi-layered mesh network used in the mask of the system of FIG. 1, in accordance with some embodiments of the present disclosure.
Figure 4E:
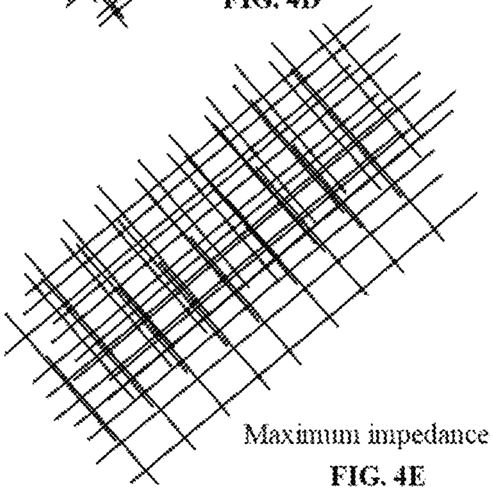
FIG. 4E is a fifth illustrative example of a multi-layered mesh network used in the mask of the system of FIG. 1, in accordance with some embodiments of the present disclosure.

Consider a grid of filtering material (layer) with average pore size of 1 micrometer. As depicted in FIG. 4A Consider 4 such grids overlaid on each other to form the mesh network 102*a*. Each layer can be moved precisely by using MEMS (actuators) technology as shown in FIG. 4B. The movement is proportional to the voltage stimulus given to MEMS actuator for that layer. As seen is the FIG. 4C, there are 4 pairs of MEMS actuators coupled with 4 layers of filter material.

Assume that activation of 1st MEMS displace the filter 1 by 20 microns overlapping other 3, 2nd MEMS actuation displaces filter 2 by 40 microns, 3rd MEMS displaces the filter by 60 microns and 4th MEMs displaces by 80 micrometer. Following table 1 depicts a typical control signal configuration and resultant air impedance of the mesh network 102*a*.

TABLE 1

| Threat | MEMS1 activation | MEMS2 activation | MEMS3 activation | MEMS4 activation | Remark |
|---|---|---|---|---|---|
| No | X | X | X | X | Whole 100 micrometer per opening - 0 impedance |
| Pollen grain | Y | X | X | X | 20% of the average hole size closed |
| Bacterial contamination n/pathogenic droplets | y | y | X | X | 40% of the average hole size closed |
| Viral/SPM contamination detected | Y | y | y | y | 80% of the average hole size closed, maximum air impedance |

Figure 5:
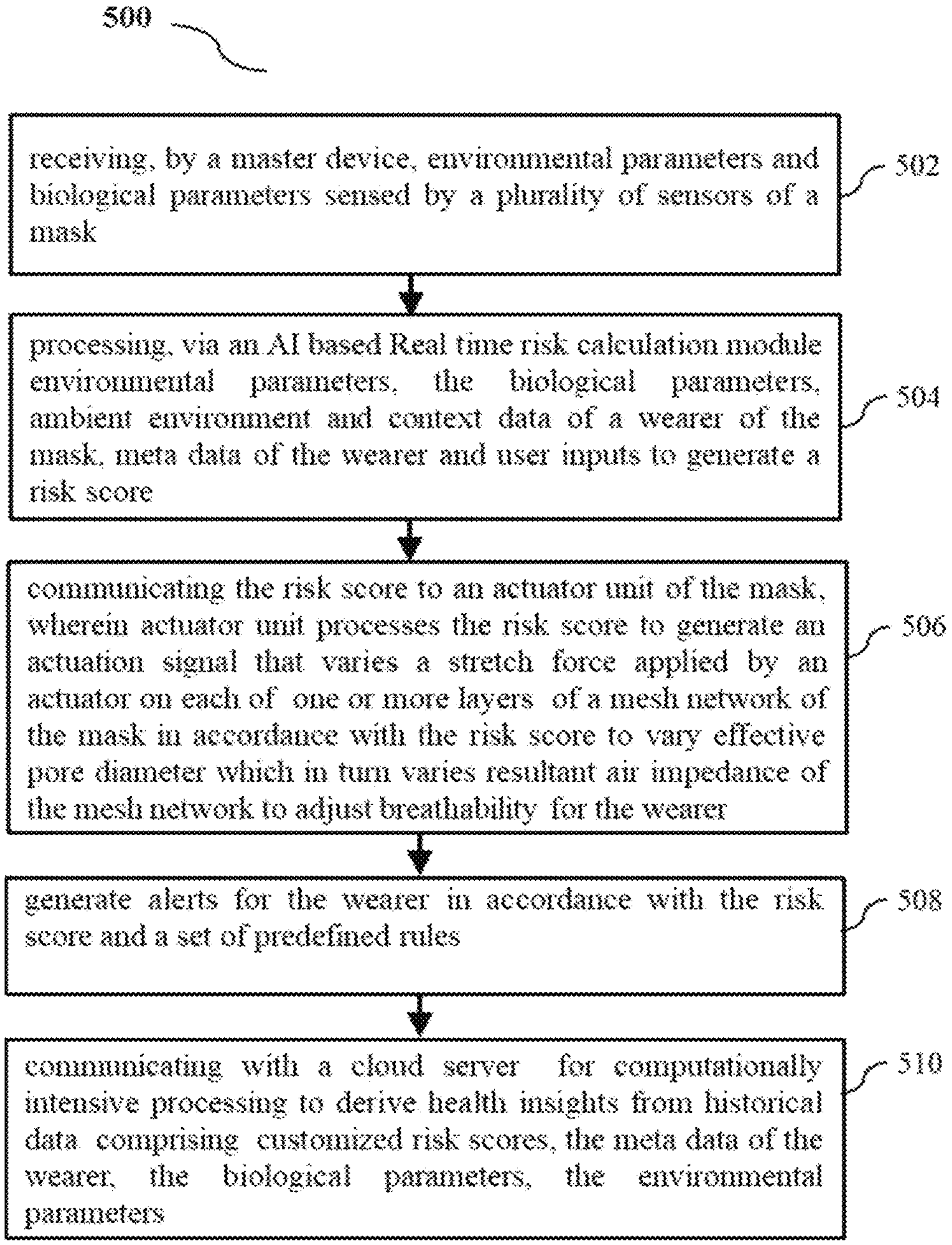
FIG. 5 is a flow diagram illustrating a method for context aware networked mask with dynamic air impedance for optimum breathability, using the system of FIG. 1, in accordance with some embodiments of the present disclosure.

FIG. 5 is a flow diagram illustrating a method 500 for context aware networked mask with dynamic air impedance for optimum breathability, using the system of FIG. 1, in accordance with some embodiments of the present disclosure.

In an embodiment, the master device 102 comprises one or more data storage devices or the memory 202 operatively coupled to the processor(s) 204 and is configured to store instructions for execution of steps of the method 500 by the processor(s) or one or more hardware processors 204. The steps of the method 500 of the present disclosure will now be explained with reference to the components or blocks of the master device 102 and the system 100 as depicted in FIG. 1 and the steps of flow diagram as depicted in FIG. 5. Although process steps, method steps, techniques or the like may be described in a sequential order, such processes, methods, and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

Referring to the steps of the method 500, at step 502 of the method 500, the one or more hardware processors 204 receive the plurality of environmental parameters and the biological parameters sensed by the plurality of sensors 102*d* of the mask 102. On receiving the sensed parameters, at step 504 of the method 500, the one or more hardware processors 204 process via the AI based Real time risk calculation module 210 implemented by the one or more hardware processors 204, the plurality of environmental parameters, the biological parameters, ambient environment and context data of a wearer of the mask, meta data of the wearer and user inputs to generate a customized risk score. In one of the embodiments the AI based Real time risk calculation module 210 can be a Deep Neural Network (DNN) pre-trained on large multi-variate time series dataset of biological sensors including CO2 sensors, temperature sensors, SPO2 and moisture sensors. Another DNN can be pre-trained on MEMS, gyroscope, mobility, location etc. time series data. Different such models can be trained as a multi-task learning model that gives all prediction from the same model. During deployment such a DNN or a set of ensemble DNN may be transfer-learned from user context and the particular geographical location, place where the user will be staying for a period. This assumes that during provisioning, the server side has an estimate of pollution, pathogen etc. levels for the location where the mask will be used initially and the combination of mask, phone, wearable etc. that user starts with. If the mask moves to a completely new geography, OR an completely new combination of mask, phone, wearable (user devices) a new updated model needs to be provisioned in the mask. An example of DNN for multivariate time-series can be ResNet. In one of the embodiments for risk calculation predefined thresholds are used and two clusters are defined for location based pathogen level [low, high] and two clusters for the user's mobility towards a given zone as [fast, slow]. For a tuple [pathogen: high, mobility:fast], the mask immediately starts actuation workflow. For the other case the mask sends alerts to user devices at different time resolutions based on the combined risk level. This can be overridden by a set of predefined rules (e.g. mask user is aware and sets a do not disturb to the mask software through phone UI). The actual provisioning of the DNN involves a capability (processing, memory, battery) based partitioning of the DNN model, where each part of the model is be mapped to the device hierarchy (eg. mask→smartphone→edge server). The server side database is asynchronously updated by the pollution/pathogen levels sent by the mask users in a geographical location, and the server averages the levels obtained from the mask-users.

At step 506 of the method 500, the one or more hardware processors 204 communicates the customized risk score to the actuator unit 102*c*2 of the mask 102. The actuator unit 102*c*2 processes the customized risk score to generate the actuation signal that varies the stretch force applied by the actuator 102*b* on each of one or more layers of the mesh network 102*a* in accordance with the customized risk score to vary effective pore size (pore diameter) of the mesh network 102*a*, which in turn varies the resultant air impedance of the mesh network 102*a*. Thus, enables adjusting breathability for the wearer.

At step 508 of the method 500, the one or more hardware processors 204 generate alerts for the wearer in accordance with the customized risk score and a set of predefined rules. The example rules are stated above at step 504 in context of AI based risk module generation/training.

At step 510 of the method 500, the one or more hardware processors 204 communicate with the cloud server 106 for computationally intensive processing to derive health insights from historical data comprising customized risk scores, the meta data of the wearer, the biological parameters, the environmental parameters. Thus, large volume of data collected over time from the smart mask and the computed risk scores, trained AL modules and analytical tools in the cloud server can health insights and predictions for the wearer, which can be provided on the master device 104 as notifications and reports.

Masks are essential survival tool in case of immune-compromised patients or in case of pandemics. One of the challenges of using mask for extended time is breathability. Less breathability leads to uncomforted and possible hypoxia. Smart masks available in the art hardly focus smartness with breathability context. The embodiments disclosed herein provide mechanism to have a dynamic impedance for breathability of mask depending on the context. Context is determined by using AI techniques with input variables such as sensors data, wearers metadata, location and so on. The system disclosed leverages capability of MEMS as actuating mechanism to manipulate the layers with uniform micro sized pores to achieve variability in breathability impedance.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means, and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A system for context aware networked smart mask with dynamic air impedance for optimum breathability, the system comprising:

- a mask comprising a base material attached with holding strings at two ends, wherein the base material holds:
  - a mesh network having one or more layers with a pore diameter associated with each of the one or more layers, wherein each of the one or more layers is held by an actuator applying a stretch force on each of the one or more layers;
  - a plurality of sensors, attached to the base material, and comprising a plurality of air quality sensors for sensing a plurality of environmental parameters and a plurality of biological sensors for sensing a plurality of biological parameters of a wearer of the mask;
  - a communication interface attached to the base material and configured to a) transmit the sensed plurality of environmental parameters and the plurality of biological parameters to a master device and b) receive a customized risk score from the master device; and
  - an actuator unit configured to process the customized risk score received from the communication module to generate an actuation signal that varies the stretch force applied by the actuator on each of the one or more layers in accordance to the customized risk score to vary resultant air impedance of the mesh network by varying an effective pore diameter to adjust breathability for the wearer;
- the master device, comprising:
  - a memory storing instructions;
  - one or more Input/Output (I/O) interfaces; and
  - one or more hardware processors coupled to the memory via the one or more I/O interfaces, wherein the one or more hardware processors are configured by the instructions to:
    - process, via an AI based Real time risk calculation module in the memory implemented by the one or more hardware processors, a) the plurality of environmental parameters, the plurality of biological parameters, ambient environment and context data of the wearer, meta data of the wearer and user inputs to generate the customized risk score,
    - wherein the AI based Real time risk calculation module comprises Deep Neural Network (DNN) pre-trained on large multi-variate time series data, wherein the DNN has learnt from wearer context and geographical location place where the wearer has stayed for a period,
    - wherein the actuator unit processes the customized risk score to generate the actuation signal that varies the stretch force applied by the actuator on each of one or more layers of the mesh network of the mask in accordance with the customized risk score to vary effective pore diameter of the mesh network, which in turn varies resultant air impedance to adjust breathability for the wearer; and
    - b) generate alerts for the wearer in accordance to the customized risk score and a set of predefined rules.

2. The system of claim 1, wherein the master device is configured to communicate with a cloud server for deriving health insights from historical data comprising customized risk scores, the meta data of the wearer, the plurality of biological parameters, the plurality of environmental parameters.

3. The system of claim 1, wherein the air quality sensors comprise pathogen sensors, pollen grain sensors, Volatile Organic Compounds (VOC) sensors, bacteria sensors, ear lobe based PPG sensors and mold sensors.

4. The system of claim 1, wherein the biological sensors comprise $CO_2$ sensors, temperature sensors, SPO2 and moisture sensors.

5. The system of claim 1, wherein the actuator is a precision actuator comprising at least one of a Micro ElectroMechanical System (MEMS), piezoelectric crystals or bimetallic strips.

6. The system of claim 1, wherein the mesh network comprises one of:

a mesh of closely knit polymer with elastic properties, wherein the effective pore diameter of the closely knit polymer increases with the increasing stretch force applied by the actuator unit allowing more air to enter the mask for increased breathability; and a multi-layered mesh, wherein layers of the mesh are overlaid on each other, and wherein the actuator unit is configured to realign the pores of each layer in accordance with the actuator control signal to vary the resultant pore size of the multi-layered mesh changing the air impedance and modulating the breathability.

7. A processor implemented method for context aware networked smart mask with dynamic air impedance for optimum breathability, the method comprising:

receiving, by one or more hardware processors of a master device, a plurality of environmental parameters and a plurality of biological parameters sensed by a plurality of sensors of a mask;

processing, via an AI based Real time risk calculation module implemented by the one or more hardware processors, the plurality of environmental parameters, the plurality of biological parameters, ambient environment and context data of a wearer of the mask, meta data of the wearer and user inputs to generate a customized risk score, wherein the AI based Real time risk calculation module comprises Deep Neural Network (DNN) pre-trained on large multi-variate time series data, wherein the DNN has learnt from wearer context and geographical location place where the wearer has stayed for a period, wherein the actuator unit processes the customized risk score to generate the actuation signal that varies the stretch force applied by the actuator on each of one or more layers of the mesh network of the mask in accordance with the customized risk score to vary effective pore diameter of the mesh network, which in turn varies resultant air impedance to adjust breathability for the wearer, communicating, via the one or more hardware processors, the customized risk score to an actuator unit of the mask, wherein actuator unit processes the customized risk score to generate an actuation signal that varies a stretch force applied by an actuator on each of one or more layers of a mesh network of the mask in accordance with the customized risk score to vary effective pore diameter of the mesh network, which in turn varies resultant air impedance to adjust breathability for the wearer; and generating, via the one or more hardware processors, alerts for the wearer in accordance with the customized risk score and a set of predefined rules.

8. The method of claim 7, wherein the method further comprising communicating with a cloud server for deriving health insights from historical data comprising customized risk scores, the meta data of the wearer, the plurality of biological parameters, the plurality of environmental parameters.

9. One or more non-transitory machine-readable information storage mediums comprising one or more instructions, which when executed by one or more hardware processors causes a method for context aware networked smart mask with dynamic air impedance for optimum breathability, the method comprising:

receiving, by one or more hardware processors of a master device, a plurality of environmental parameters and a plurality of biological parameters sensed by a plurality of sensors of a mask;

processing, via an AI based Real time risk calculation module implemented by the one or more hardware processors, the plurality of environmental parameters, the plurality of biological parameters, ambient environment and context data of a wearer of the mask, meta data of the wearer and user inputs to generate a customized risk score, wherein the AI based Real time risk calculation module comprises Deep Neural Network (DNN) pre-trained on large multi-variate time series data, wherein the DNN has learnt from wearer context and geographical location place where the wearer has stayed for a period, processing, via the one or more hardware processors and an actuator unit, the customized risk score to generate an actuation signal that varies the stretch force applied by an actuator on each of one or more layers of the mesh network of the mask in accordance with the customized risk score to vary effective pore diameter of the mesh network, which in turn varies resultant air impedance to adjust breathability for the wearer;

and generating, via the one or more hardware processors, alerts for the wearer in accordance with the customized risk score and a set of predefined rules.

10. The one or more non-transitory machine-readable information storage mediums of claim 9, further comprising communicating with a cloud server for deriving health insights from historical data comprising customized risk scores, the meta data of the wearer, the plurality of biological parameters, the plurality of environmental parameters.

* * * * *